(12) United States Patent
Marshall et al.

(10) Patent No.: US 12,343,200 B2
(45) Date of Patent: Jul. 1, 2025

(54) INTRAVASCULAR ULTRASOUND SYSTEMS, CATHETERS, AND METHODS WITH A MANUAL PULLBACK ARRANGEMENT

(71) Applicant: Boston Scientific SciMed, Inc., Maple Grove, MN (US)

(72) Inventors: John D. Marshall, Los Gatos, CA (US); Peter Thornton, Jr., Los Altos, CA (US); Lewis J. Thomas, III, Palo Alto, CA (US); Isaac J. Zacharias, Pleasanton, CA (US); Gaylin Mildred Yee, Newark, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 440 days.

(21) Appl. No.: 16/717,920

(22) Filed: Dec. 17, 2019

(65) Prior Publication Data

US 2020/0121280 A1 Apr. 23, 2020

Related U.S. Application Data

(62) Division of application No. 15/285,342, filed on Oct. 4, 2016, now abandoned.
(Continued)

(51) Int. Cl.
*A61B 8/12* (2006.01)
*A61B 8/00* (2006.01)
(Continued)

(52) U.S. Cl.
CPC .............. *A61B 8/12* (2013.01); *A61B 8/0891* (2013.01); *A61B 8/14* (2013.01); *A61B 8/4245* (2013.01); *A61B 8/445* (2013.01); *A61B 8/4483* (2013.01)

(58) Field of Classification Search
CPC ......... A61B 5/318; A61B 8/0891; A61B 8/12; A61B 8/14; A61B 8/4245; A61B 8/445; A61B 8/4483
See application file for complete search history.

(56) References Cited

U.S. PATENT DOCUMENTS 3,838,688 A 10/1974 May et al.
4,593,699 A 6/1986 Poncy et al.
(Continued)

FOREIGN PATENT DOCUMENTS

DE 4344312 A1 7/1994
DE 19619774 A1 11/1997
(Continued)

OTHER PUBLICATIONS

Les Schaevitz, "Finding the right sensor for linear displacement," Jul. 8, 2004, MachineDesign, pp. 1-14 (Year: 2004).*
(Continued)

*Primary Examiner* — Chao Sheng
*Assistant Examiner* — Maria Christina Talty
(74) *Attorney, Agent, or Firm* — Seager, Tufte & Wickhem, LLP

(57) ABSTRACT

A catheter assembly for an ultrasound system can include an integrated pullback arrangement. For example, the catheter assembly can include a telescoping pullback section having a first telescope, a second telescope, a distal grip coupling one of the first or second telescope to the distal sheath of the distal section, and a proximal grip coupled to another of the first or second telescope so that the first telescope can be retracted into the second telescope and a sensor to determine a position of the first telescope. Another example includes the sensor and a pullback slider arrangement having a housing defining a slit, a coupler disposed within the housing, and a slider handle extending through the slit and
(Continued)

coupled to the coupler. In another example, the coupler and housing can be gripped and slid relative to each other.

10 Claims, 6 Drawing Sheets

Related U.S. Application Data

(60) Provisional application No. 62/239,736, filed on Oct. 9, 2015.

(51) Int. Cl.
*A61B 8/08* (2006.01)
*A61B 8/14* (2006.01)

(56) References Cited

U.S. PATENT DOCUMENTS

| | | | |
|---|---|---|---|
| 4,708,125 A | 11/1987 | Miketi et al. | |
| 4,771,774 A | 9/1988 | Simpson et al. | |
| 4,794,931 A | 1/1989 | Yock | |
| 4,802,487 A | 2/1989 | Martin et al. | |
| 4,841,977 A | 6/1989 | Griffith et al. | |
| 4,870,970 A | 10/1989 | Gray et al. | |
| 4,917,097 A | 4/1990 | Proudian et al. | |
| 4,951,677 A | 8/1990 | Crowley et al. | |
| 5,000,185 A | 3/1991 | Yock | |
| 5,002,553 A | 3/1991 | Shiber | |
| 5,019,189 A | 5/1991 | Kumara et al. | |
| 5,048,529 A | 9/1991 | Blumenthal | |
| 5,105,819 A | 4/1992 | Wollschlaeger et al. | |
| 5,107,844 A | 4/1992 | Kami et al. | |
| 5,115,814 A | 5/1992 | Griffith et al. | |
| 5,125,410 A | 6/1992 | Misono et al. | |
| 5,178,148 A | 1/1993 | Lacoste et al. | |
| 5,203,338 A | 4/1993 | Jang | |
| 5,211,176 A | 5/1993 | Ishiguro et al. | |
| 5,318,576 A | 6/1994 | Plassche et al. | |
| 5,321,501 A | 6/1994 | Swanson et al. | |
| 5,358,485 A | 10/1994 | Vance et al. | |
| 5,360,432 A | 11/1994 | Shturman | |
| 5,366,464 A | 11/1994 | Belknap | |
| 5,373,849 A | 12/1994 | Maroney et al. | |
| 5,383,460 A | 1/1995 | Jang et al. | |
| 5,398,690 A | 3/1995 | Batten et al. | |
| 5,485,846 A | 1/1996 | Webler et al. | |
| 5,488,955 A | 2/1996 | Dias | |
| 5,490,859 A | 2/1996 | Mische et al. | |
| 5,497,776 A | 3/1996 | Yamazaki et al. | |
| 5,546,947 A | 8/1996 | Yagami et al. | |
| 5,551,432 A | 9/1996 | Iezzi et al. | |
| 5,554,163 A | 9/1996 | Shturman | |
| 5,569,179 A | 10/1996 | Adrian | |
| 5,592,942 A | 1/1997 | Webler et al. | |
| 5,651,364 A | 7/1997 | Yock | |
| 5,759,153 A | 6/1998 | Webler et al. | |
| 5,762,599 A | 6/1998 | Sohn | |
| 5,797,858 A | 8/1998 | Rourke | |
| 5,827,313 A | 10/1998 | Ream | |
| 5,833,616 A | 11/1998 | Gruner et al. | |
| 5,865,178 A | 2/1999 | Yock | |
| 5,865,748 A | 2/1999 | Co et al. | |
| 5,897,567 A | 4/1999 | Ressemann et al. | |
| 5,932,035 A | 8/1999 | Koger et al. | |
| 5,957,941 A | 9/1999 | Ream | |
| 5,967,984 A * | 10/1999 | Chu | A61B 8/12 600/439 |
| 6,004,271 A | 12/1999 | Moore | |
| 6,013,030 A | 1/2000 | Webler et al. | |
| 6,193,736 B1 | 2/2001 | Webler et al. | |
| 6,319,227 B1 | 11/2001 | Mansouri-Ruiz | |
| 6,398,755 B1 | 6/2002 | Belef et al. | |
| 6,413,222 B1 | 7/2002 | Pantages et al. | |
| 6,454,717 B1 | 9/2002 | Pantages et al. | |
| 6,475,224 B1 | 11/2002 | Pantages et al. | |
| 6,517,528 B1 * | 2/2003 | Pantages | A61B 8/12 600/459 |
| 6,945,938 B2 | 9/2005 | Grunwald | |
| 7,004,911 B1 | 2/2006 | Tu et al. | |
| 7,246,959 B2 | 7/2007 | Nakatani | |
| 7,306,561 B2 | 12/2007 | Sathyanarayana | |
| 2002/0188225 A1 * | 12/2002 | White | A61B 8/4461 600/585 |
| 2003/0187369 A1 * | 10/2003 | Lewis | A61B 5/1076 600/587 |
| 2005/0043618 A1 * | 2/2005 | Mansouri-Ruiz | A61B 8/4461 600/435 |
| 2006/0052700 A1 | 3/2006 | Svanerudh | |
| 2006/0084911 A1 * | 4/2006 | Belef | A61B 46/10 604/95.01 |
| 2006/0100522 A1 | 5/2006 | Yuan et al. | |
| 2006/0106320 A1 | 5/2006 | Barbato | |
| 2006/0173350 A1 | 8/2006 | Yuan et al. | |
| 2006/0253028 A1 | 11/2006 | Lam et al. | |
| 2007/0000498 A1 | 1/2007 | Glynn et al. | |
| 2007/0016054 A1 | 1/2007 | Cao et al. | |
| 2007/0038111 A1 | 2/2007 | Rehrig et al. | |
| 2008/0004530 A1 | 1/2008 | Feldman et al. | |
| 2008/0021275 A1 | 1/2008 | Tearney et al. | |
| 2008/0051660 A1 | 2/2008 | Kakadaris et al. | |
| 2008/0146942 A1 | 6/2008 | Dala-Krishna | |
| 2008/0167560 A1 | 7/2008 | Thornton | |
| 2009/0156941 A1 * | 6/2009 | Moore | A61B 8/4461 600/467 |
| 2009/0234319 A1 | 9/2009 | Marksteiner | |
| 2009/0270737 A1 | 10/2009 | Thornton | |
| 2009/0318003 A1 * | 12/2009 | Hossack | A61B 8/445 439/299 |
| 2010/0249588 A1 | 9/2010 | Knight | |
| 2014/0142436 A1 * | 5/2014 | Hutchins | A61B 5/0084 600/478 |
| 2014/0180142 A1 | 6/2014 | Millett et al. | |
| 2015/0182190 A1 * | 7/2015 | Hiltner | A61B 8/12 600/463 |

FOREIGN PATENT DOCUMENTS

| | | |
|---|---|---|
| EP | 163502 A2 | 12/1985 |
| EP | 244058 A1 | 11/1987 |
| EP | 0266858 A1 | 5/1988 |
| EP | 397459 A1 | 11/1990 |
| EP | 0626152 A1 | 11/1994 |
| EP | 1076513 A1 | 2/2001 |
| FR | 2543817 A1 | 10/1984 |
| JP | 1066696 A | 3/1998 |
| WO | 9001300 A1 | 2/1990 |
| WO | 9115154 A1 | 10/1991 |
| WO | 9203095 A1 | 3/1992 |
| WO | 9219930 A1 | 11/1992 |
| WO | 9316642 A1 | 9/1993 |
| WO | 9400052 A1 | 1/1994 |
| WO | 9411038 A1 | 5/1994 |
| WO | 9732182 A1 | 9/1997 |
| WO | 20070103726 A2 | 9/2007 |
| WO | WO-2014134275 A2 * | 9/2014 ......... A61M 25/002 |

OTHER PUBLICATIONS

International Search Report and Written Opinion for International Application No. PCT/US2016/055358, mailed Mar. 15, 2017, 19 pages.

* cited by examiner

INTRAVASCULAR ULTRASOUND SYSTEMS, CATHETERS, AND METHODS WITH A MANUAL PULLBACK ARRANGEMENT

CROSS-REFERENCE TO RELATED APPLICATIONS

This application is a divisional of U.S. patent application Ser. No. 15/285,342, filed Oct. 4, 2016, which claims the benefit under 35 U.S.C. § 119(e) of U.S. Provisional Patent Application Ser. No. 62/239,736, filed Oct. 9, 2015, both which are incorporated herein by reference.

TECHNICAL FIELD

The present invention is directed to the area of ultrasound imaging systems and methods of making and using the systems. The present invention is also directed to an ultrasound imaging system and catheter that includes a manual pullback arrangement, as well as methods of making and using the ultrasound systems and catheters.

BACKGROUND

Ultrasound devices insertable into patients have proven diagnostic capabilities for a variety of diseases and disorders. For example, intravascular ultrasound ("IVUS") imaging systems have been used as an imaging modality for diagnosing blocked blood vessels and providing information to aid medical practitioners in selecting and placing stents and other devices to restore or increase blood flow. IVUS imaging systems have been used to diagnose atheromatous plaque build-up at particular locations within blood vessels. IVUS imaging systems can be used to determine the existence of an intravascular obstruction or stenosis, as well as the nature and degree of the obstruction or stenosis. IVUS imaging systems can be used to visualize segments of a vascular system that may be difficult to visualize using other intravascular imaging techniques, such as angiography, due to, for example, movement (e.g., a beating heart) or obstruction by one or more structures (e.g., one or more blood vessels not desired to be imaged). IVUS imaging systems can be used to monitor or assess ongoing intravascular treatments, such as angiography and stent placement in real (or almost real) time. Moreover, IVUS imaging systems can be used to monitor one or more heart chambers.

IVUS imaging systems have been developed to provide a diagnostic tool for visualizing a variety of diseases or disorders. An IVUS imaging system can include a control module (with a pulse generator, an image processor, and a monitor), a catheter, and one or more transducers disposed in the catheter. The transducer-containing catheter can be positioned in a lumen or cavity within, or in proximity to, a region to be imaged, such as a blood vessel wall or patient tissue in proximity to a blood vessel wall. The pulse generator in the control module generates electrical signals that are delivered to the one or more transducers and transformed to acoustic signals that are transmitted through patient tissue. Reflected signals of the transmitted acoustic signals are absorbed by the one or more transducers and transformed to electric signals. The transformed electric signals are delivered to the image processor and converted to an image displayable on the monitor.

Intracardiac echocardiography ("ICE") is another ultrasound imaging technique with proven capabilities for use in diagnosing intravascular diseases and disorders. ICE uses acoustic signals to image patient tissue. Acoustic signals emitted from an ICE imager disposed in a catheter are reflected from patient tissue and collected and processed by a coupled ICE control module to form an image. ICE imaging systems can be used to image tissue within a heart chamber.

BRIEF SUMMARY

One embodiment is a catheter assembly for an ultrasound system that includes a distal section having a distal sheath; a proximal extension having a proximal sheath; and a telescoping pullback section between the distal section and the proximal extension and having a first telescope, a second telescope, a distal grip coupling one of the first or second telescope to the distal sheath of the distal section, and a proximal grip coupled to another of the first or second telescope. The first telescope can be retracted into the second telescope by gripping the distal and proximal grips and manually moving the distal and proximal grips away from each other. The catheter assembly also includes a sensor disposed along the telescoping pullback section to determine a position of the first telescope as the first telescope is moved relative to the sensor; an elongated, rotatable driveshaft having a proximal end and a distal end and extending along the distal section, proximal extension, and telescoping pullback section with the proximal end configured and arranged for coupling to a motordrive for rotating the driveshaft; an imaging device coupled to the distal end of the driveshaft with rotation of the driveshaft causing a corresponding rotation of the imaging device, the imaging device including at least one transducer for transforming applied electrical signals to acoustic signals and also for transforming received echo signals to electrical signals; and at least one conductor extending along the distal section, proximal extension, and telescoping pullback section and coupled to the imaging device for carrying the electrical signals.

In at least some embodiments, the first telescope is distal to the second telescope. In at least some embodiments, the catheter assembly further includes a housing disposed at a distal end of the second telescope with the sensor disposed in the housing. In at least some embodiments, the proximal grip is disposed at a distal end of the second telescope. In at least some embodiments, the sensor is disposed in the proximal grip.

In at least some embodiments, the sensor is an optical sensor and the first telescope includes a set of alternating stripes of different colors detectable by the optical sensor to determine a position of the first telescope. In at least some embodiments, the sensor is a resistive, capacitive, inductive, or magnetic sensor. In at least some embodiments, the proximal grip includes at least one control button, where actuation of one of the at least one control button provides a signal related to a pullback procedure.

Another embodiment is a catheter assembly for an ultrasound system that includes a distal section having a distal sheath; a proximal extension having a proximal sheath; and a pullback slider arrangement disposed between the distal section and the proximal extension. The pullback slider arrangement includes a housing defining a slit, a coupler disposed within the housing, and a slider handle extending through the slit and coupled to the coupler, wherein the slider handle and the coupler can be manually slid along the slit in the housing. The catheter assembly also includes a sensor disposed within the housing of the pullback slider arrangement to determine a position of the coupler within the housing; an elongated, rotatable driveshaft having a proximal end and a distal end and extending along the distal section, proximal extension, and pullback slider arrangement with the proximal end configured and arranged for coupling to a motordrive for rotating the driveshaft, where the coupler of the pullback slider arrangement is coupled to the rotatable driveshaft to manually move the rotatable driveshaft backwards and forwards by moving the slider handle; an imaging device coupled to the distal end of the driveshaft with rotation of the driveshaft causing a corresponding rotation of the imaging device, the imaging device including at least one transducer configured and arranged for transforming applied electrical signals to acoustic signals and also for transforming received echo signals to electrical signals; and at least one conductor extending along the distal section, proximal extension, and telescoping pullback section and coupled to the imaging device for carrying the electrical signals.

In at least some embodiments, the housing of the pullback slider arrangement includes at least one control button, where actuation of one of the at least one control button provides a signal related to a pullback procedure. In at least some embodiments, the sensor is an optical, resistive, capacitive, inductive, or magnetic sensor. In at least some embodiments, the sensor is a potentiometer. In at least some embodiments, the sensor is a capacitive sensor and includes a first plate and a second plate that is coupled to the coupler of the pullback slider arrangement so that capacitance between the first and second plates varies with position of the coupler. In at least some embodiments, the sensor is an inductive sensor and includes a coil and a magnetic material that is coupled to the coupler of the pullback slider arrangement and moves with the coupler so that inductance of the coil varies with position of the coupler.

In at least some embodiments, the sensor is an optical sensor coupled to the coupler and the pullback slider arrangement includes a set of alternating stripes of different colors detectable by the optical sensor and disposed in the housing to determine a position of the coupler. In at least some embodiments, the sensor is a magnetic sensor coupled to the coupler and the pullback slider arrangement includes a set of alternating stripes of magnetic materials detectable by the magnetic sensor and disposed in the housing to determine a position of the coupler.

Yet another embodiment is a catheter assembly for an ultrasound system that includes a distal section having a distal sheath; a proximal extension having a proximal sheath; and a pullback slider arrangement disposed between the distal section and the proximal extension. The pullback slider arrangement includes a housing defining an opening and a coupler disposed partially within the housing and extending through the opening in the housing, where the coupler can slide relative to the housing to change a size of a portion of the coupler disposed within the housing. The catheter assembly further includes a sensor disposed within the housing of the pullback slider arrangement to determine a position of the coupler relative to the housing; an elongated, rotatable driveshaft having a proximal end and a distal end and extending along the distal section, proximal extension, and pullback slider arrangement, where the proximal end is configured and arranged for coupling to a motordrive for rotating the driveshaft, where the coupler of the pullback slider arrangement is coupled to the rotatable driveshaft to manually move the rotatable driveshaft backwards and forwards by moving the slider handle; an imaging device coupled to the distal end of the driveshaft with rotation of the driveshaft causing a corresponding rotation of the imaging device, the imaging device including at least one transducer configured and arranged for transforming applied electrical signals to acoustic signals and also for transforming received echo signals to electrical signals; and at least one conductor extending along the distal section, proximal extension, and telescoping pullback section and coupled to the imaging device for carrying the electrical signals.

In at least some embodiments, the sensor is an optical sensor coupled to the housing and the coupler includes a set of alternating stripes of different colors detectable by the optical sensor to determine a position of the coupler. In at least some embodiments, the sensor is a magnetic sensor coupled to the housing and the coupler includes a set of alternating stripes of magnetic materials detectable by the magnetic sensor to determine a position of the coupler. In at least some embodiments, the housing defines a slit and the coupler includes a flush port that extends out of the slit.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of ultrasound imaging systems and methods of making and using the systems. The present invention is also directed to an ultrasound imaging system and catheter that includes a manual pullback arrangement, as well as methods of making and using the ultrasound systems and catheters.

Suitable ultrasound imaging systems utilizing catheters include, for example, intravascular ultrasound ("IVUS") and intracardiac echocardiography ("ICE") systems. These systems may include one or more transducers disposed on a distal end of a catheter configured and arranged for percutaneous insertion into a patient. Examples of IVUS imaging systems with catheters are found in, for example, U.S. Pat. Nos. 6,945,938; 7,246,959; and 7,306,561; as well as U.S. Patent Application Publication Nos. 2006/0100522; 2006/0106320; 2006/0173350; 2006/0253028; 2007/0016054; and 2007/0038111; all of which are incorporated herein by reference in their entireties.

In at least some embodiments, the imaging core may move longitudinally (i.e., translate) along the blood vessel within which the catheter is inserted to obtain a series of images along the axial length of the blood vessel. In at least some embodiments, during an imaging procedure the imaging core is retracted (i.e., pulled back) along the longitudinal length of the catheter. In many conventional IVUS imaging systems this pullback procedure is automated with a pullback arrangement coupled to a motor to pull back the imaging core when directed by the clinician. It may be desirable, however, to manually perform the pullback. An IVUS catheter with an integrated pullback arrangement can be used for manually performing a pullback procedure. In at least some embodiments, the IVUS imaging system may also be capable of performing an automated pullback procedure. In other embodiments, the IVUS imaging system may only be capable of a manual pullback procedure.

Figure 1:
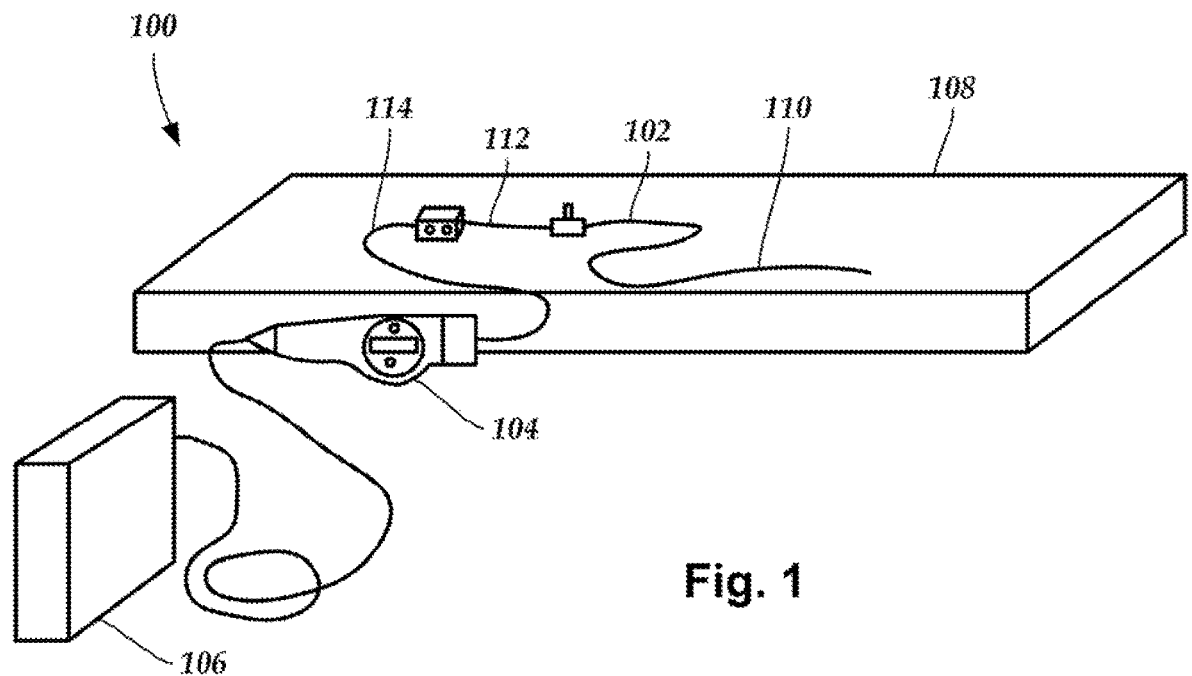
FIG. 1 is a schematic view of one embodiment of an intravascular ultrasound imaging system, according to the invention.

FIG. 1 illustrates an IVUS imaging system 100 having an IVUS catheter 102 with an integrated pullback arrangement, a motordrive 104, and an imaging module 106. At least some of the components of the IVUS imaging system 100 are placed near an operating table 108. In at least some embodiments, the integrated pullback arrangement of the IVUS catheter 102 is a manual pullback arrangement to allow a clinician to manually control the pullback.

Figure 2:
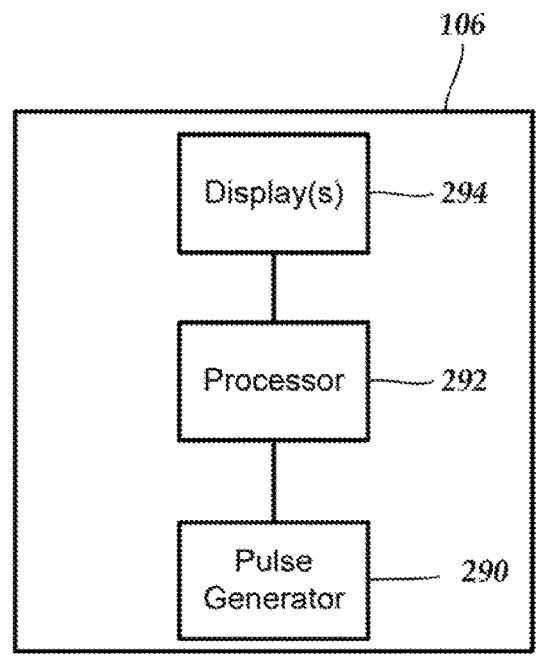
FIG. 2 is a schematic side view of one embodiment of an imaging module of an intravascular ultrasound imaging system, according to the invention.

The imaging module 106 may include, for example, a processor 292, a pulse generator 290, and one or more displays 294, as illustrated in FIG. 2. In at least some embodiments, the pulse generator 290 generates electric signals that may be input to one or more transducers (312 in FIG. 3) disposed in the catheter 102 so that the one or more transducers generate acoustic signals for imaging. In at least some embodiments, the processor 292 directs the motordrive 104 (FIG. 1) to rotate an imaging core (306 in FIG. 3) disposed in the catheter 102.

In at least some embodiments, electrical signals transmitted from the one or more transducers (312 in FIG. 3) and generated in response to acoustic echoes may be input to the processor 292 for processing. In at least some embodiments, the processed electrical signals from the one or more transducers (312 in FIG. 3) may be displayed as one or more images on the one or more displays 294. In at least some embodiments, the processor 292 may also be used to control the functioning of one or more of the other components of the imaging module 106 or imaging system 100. For example, the processor 292 may be used to control at least one of the frequency or duration of the electrical signals transmitted from the pulse generator 290, the rotation rate of the imaging core (306 in FIG. 3) by the motordrive 104, or one or more properties of one or more images formed on the one or more displays 294.

Figure 3:
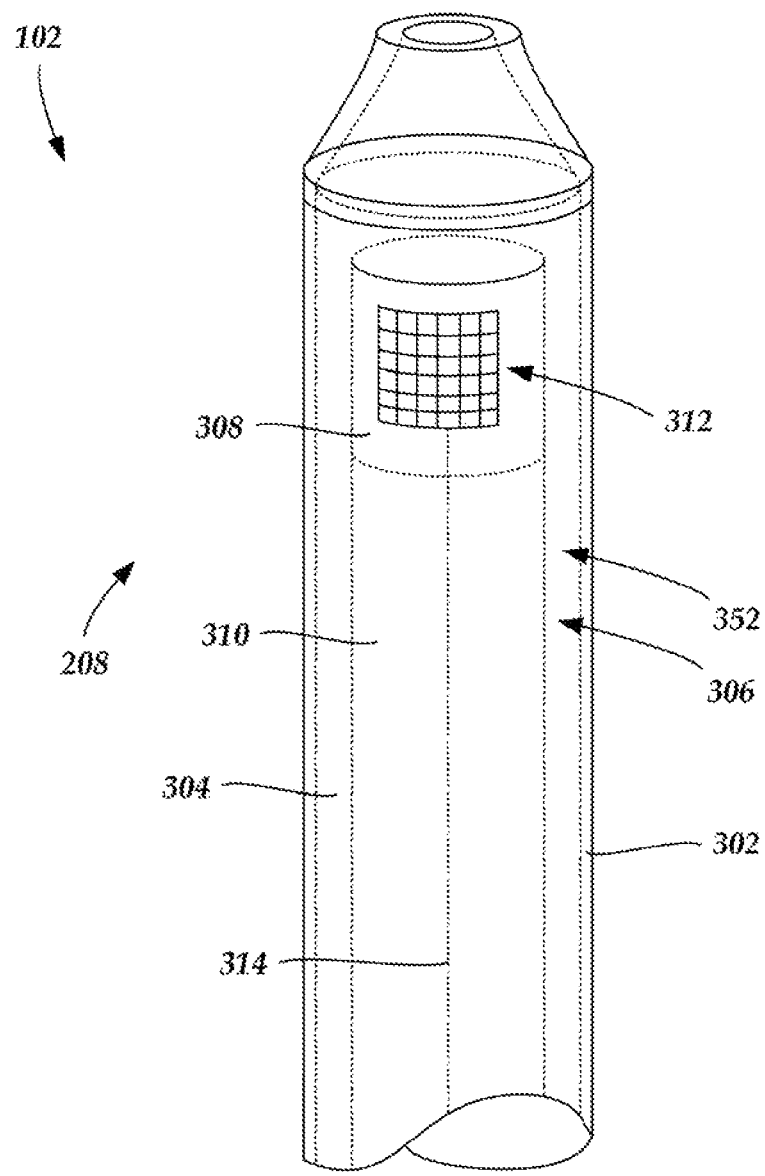
FIG. 3 is a schematic perspective view of one embodiment of a distal end of the catheter shown in FIG. 1 with an imaging core disposed in a lumen defined in the catheter, according to the invention.

FIG. 3 is a schematic perspective view of one embodiment of the distal end 208 of the catheter 102. The catheter 102 includes a sheath 302 having a distal portion 352 and a proximal portion (not shown). The sheath 302 defines a lumen 304 extending along the sheath. An imaging core 306 is disposed in the lumen 304. The imaging core 306 includes an imaging device 308 coupled to a distal end of a driveshaft 310.

The sheath 302 may be formed from any flexible, biocompatible material suitable for insertion into a patient. Examples of suitable materials include, for example, polyethylene, polyurethane, plastic, spiral-cut stainless steel, nitinol hypotube, and the like or combinations thereof.

One or more transducers 312 may be mounted to the imaging device 308 and employed to transmit and receive acoustic signals. In a preferred embodiment (as shown in FIG. 3), an array of transducers 312 are mounted to the imaging device 308. In other embodiments, a single transducer may be employed. In at least some embodiments, multiple transducers in an irregular-array may be employed. Any number of transducers 312 can be used. For example, there can be one, two, three, four, five, six, seven, eight, nine, ten, twelve, fifteen, sixteen, twenty, twenty-five, fifty, one hundred, five hundred, one thousand, or more transducers. As will be recognized, other numbers of transducers may also be used.

The one or more transducers 312 may be formed from one or more known materials capable of transforming applied electrical signals into pressure distortions on the surface of the one or more transducers 312, and vice versa. Examples of suitable materials include piezoelectric ceramic materials, piezocomposite materials, piezoelectric plastics, barium titanates, lead zirconate titanates, lead metaniobates, polyvinylidenefluorides, and the like.

The pressure distortions on the surface of the one or more transducers 312 form acoustic signals of a frequency based on the resonant frequencies of the one or more transducers 312. The resonant frequencies of the one or more transducers 312 may be affected by the size, shape, and material used to form the one or more transducers 312. The one or more transducers 312 may be formed in any shape suitable for positioning within the catheter 102 and for propagating acoustic signals of a desired frequency in one or more selected directions. For example, transducers may be disc-shaped, block-shaped, rectangular-shaped, oval-shaped, and the like. The one or more transducers may be formed in the desired shape by any process including, for example, dicing, dice and fill, machining, microfabrication, and the like.

In at least some embodiments, the one or more transducers 312 can be used to form a radial cross-sectional image of a surrounding space. Thus, for example, when the one or more transducers 312 are disposed in the catheter 102 and inserted into a blood vessel of a patient, the one more transducers 312 may be used to form a composite image of the walls of the blood vessel and tissue surrounding the blood vessel by stitching together a plurality of individual image frames.

The imaging core 306 is rotated about a longitudinal axis of the catheter 102 while being disposed in the distal portion 352 of the sheath 302. As the imaging core 306 rotates, the one or more transducers 312 emit acoustic signal in different radial directions. When an emitted acoustic signal with sufficient energy encounters one or more medium boundaries, such as one or more tissue boundaries, a portion of the emitted acoustic signal is reflected back to the emitting transducer as an echo signal. Each echo signal that reaches a transducer with sufficient energy to be detected is transformed to an electrical signal in the receiving transducer. The one or more transformed electrical signals are transmitted to the imaging module (106 in FIG. 1) where the processor 292 (FIG. 2) processes the electrical-signal characteristics to generate a displayable image frame of the imaged region based, at least in part, on a collection of information from each of the acoustic signals transmitted and the echo signals received.

In at least some embodiments, the rotation of the one or more transducers 312 is driven by the motordrive 104 (FIG. 1) via the driveshaft 310 extending along the catheter 102. The motordrive 104 is coupled to the proximal end of the catheter 102 and the driveshaft 310 and rotates the driveshaft. Any suitable motordrive 104 can be used including those described in U.S. Pat. Nos. 6,004,271; 6,319,227; 6,413,222; 6,454,717; 6,475,224; and 6,517,528; and U.S. Patent Application Publication No. 2008/0167560, all of which are incorporated herein by reference in their entireties. Another suitable motordrive is the MDU 5+ Motordrive from Boston Scientific™ Corporation (Natick, MA). It will be recognized that some of these motordrives may also incorporate automated pullback systems that may also be useful with the manual pullback arrangement described herein to provide clinicians with a choice between manual or automated pullback.

As the one or more transducers 312 rotate about the longitudinal axis of the catheter 102 emitting acoustic signals, a plurality of image frames are formed that collectively form a composite radial cross-sectional image of a portion of the region surrounding the one or more transducers 312, such as the walls of a blood vessel of interest and the tissue surrounding the blood vessel. In at least some embodiments, one or more of the image frames can be displayed on the one or more displays 294 (FIG. 2). In at least some embodiments, the radial cross-sectional composite image can be displayed on the one or more displays 294 (FIG. 2).

The quality of imaging at different depths from the one or more transducers 312 may be affected by one or more factors including, for example, bandwidth, transducer focus, beam pattern, as well as the frequency of the acoustic signal. The frequency of the acoustic signal output from the one or more transducers 312 may also affect the penetration depth of the acoustic signal output from the one or more transducers 312. In general, as the frequency of an acoustic signal is lowered, the depth of the penetration of the acoustic signal within patient tissue increases. In at least some embodiments, the IVUS imaging system 100 operates within a frequency range of 5 MHz to 60 MHz.

One or more conductors 314 (for example, wires, cables, traces, or the like) electrically couple the transducers 312 to the imaging module 106 (FIG. 1). In at least some embodiments, the one or more conductors 314 extend along the driveshaft 310.

The imaging device 308 is inserted in the lumen of the catheter 102. In at least some embodiments, the catheter 102 (and imaging device 308) may be inserted percutaneously into a patient via an accessible blood vessel, such as the femoral artery or vein, at a site remote from a target imaging location. The catheter 102 may then be advanced through patient vasculature to the target imaging location, such as a portion of a selected blood vessel (e.g., a peripheral blood vessel, a coronary blood vessel, or other blood vessel), or one or more chambers of the patient's heart.

Returning to FIG. 1, the IVUS catheter 102 has a distal section 110, a telescoping pullback section 112, and a proximal extension 114. The distal section 110 includes the rotating imaging core and a portion of the rotating driveshaft surrounded by a stationary distal sheath. A portion of the distal section 110 is the part of the IVUS catheter 102 that is inserted into the patient. The proximal extension 114 includes a portion of the rotating driveshaft and a stationary proximal sheath. The proximal extension 114 of the catheter is coupled to the motordrive 104.

Figure 4:
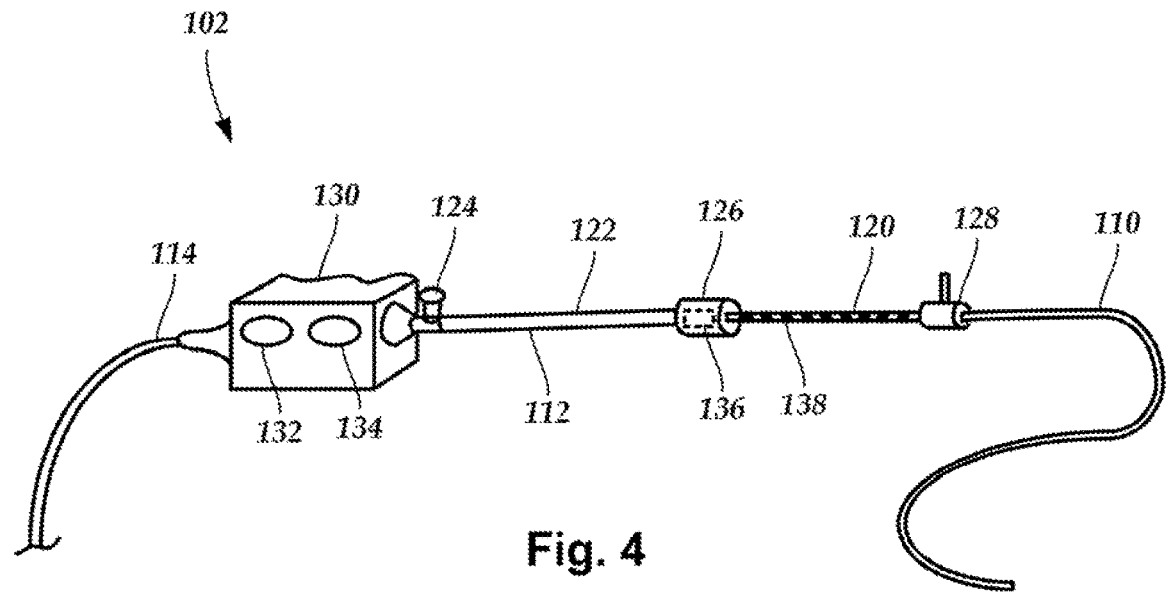
FIG. 4 is a schematic side view of a portion of one embodiment of a catheter with a telescoping pullback section, according to the invention.

FIG. 4 illustrates a portion of one embodiment of an IVUS catheter and integrated pullback arrangement. The telescoping pullback section 112 is disposed between the distal section 110 and the proximal extension 114 and makes use of a first telescope 120 sliding within a second telescope 122 to cause the rotating imaging core to slide proximally or distally within the distal sheath. In the illustrated embodiments, the first telescope 120 is distal to the second telescope, but it will be understood that this arrangement could be reversed with the first telescope proximal to the second telescope. The driveshaft extends along the telescoping pullback section 112 including through the first and second telescopes 120, 122. It will be understood that the driveshaft can be a single unitary structure or can include multiple elements that are coupled together.

In at least some embodiments, one or both of the telescoping pullback section 112 and distal section 110 can be flushed with sterile saline via a port 124 disposed within the telescoping section. In FIG. 4, the flush port 124 is depicted at the proximal end of the second telescope 122, but it will be understood that the port can be placed elsewhere along the telescoping pullback section 112 or distal section 110. The first and second telescopes 120, 122 join at a housing 126 which optionally contains a seal to allow the telescoping action without leakage of the saline.

The telescoping pullback section 112 also includes a distal grip 128 coupling one of the telescopes 120, 122 to the distal sheath of the distal section 110 and a proximal grip 130 coupled to the other of the telescopes 120, 122. During pullback, the distal and proximal grips 128, 130 are gripped and moved away from each other (for example, the distal grip 128 is held stationary while the proximal grip 130 is pulled back). This action causes the imaging device (e.g., one or more transducers) situated at the distal tip of the imaging core to move in a proximal direction within the distal section 110 to image successively more proximal sections of the vascular anatomy. This arrangement allows for manual pullback instead of the automated pullback of conventional IVUS imaging systems.

The telescoping pullback section 112 of the catheter 102 also includes a sensor 136 capable of providing accurate pullback position information to the imaging module 106 (FIG. 1). For example, the sensor 136 can indicate a position of the first telescope 120 relative to the second telescope 122. In the embodiment of FIG. 4, the sensor 136 can be disposed, for example, in the housing 126 or in the proximal grip 130. Any suitable sensor 136 can be used including, but not limited to, resistive, capacitive, magnetic, optical or other sensors that can sense the position of the first telescope 120 relative to the second telescope 122 or sense the position of the one of the telescopes 120, 122 to a fixed position. Examples of sensors are described below.

In the illustrated embodiment of FIG. 4, the sensor 136 can observe stripes 138 on the first telescope 120. For example, these stripes 138 may be alternating bands of dark and light pigment to be read by an optical sensor or may be stripes of alternating magnetically polarized material to be read by a magnetic sensor. Communications between the sensor 136 and the proximal grip 130 are made via an electrical cable or wire contiguous with the second telescope 122. The cable or wire may be disposed alongside the second telescope or may be embedded in the wall of the second telescope or may be connected via some other path away from the second telescope.

The proximal grip 130 may also incorporate one or more control buttons 132, 134. The control buttons 132, 134 may be operated during pullback to individually control a function such as "imaging start/stop", "pullback recording start/stop", "zero position", or "place bookmark".

Returning to FIG. 1, the proximal extension 114 includes a portion of the rotating driveshaft and the conductor (for conveying imaging signals between the imaging module and the ultrasound transducers) surrounded by a stationary sheath. The proximal extension 114 includes a connector to join it to the motordrive 104 and it may be larger in diameter than the distal portion 110 of the catheter. In some embodiments, the proximal extension 114 also supports a stationary (nonrotating) multi-conductor electrical cable joined to the stationary sheath to convey signals from the position sensor 136 (FIG. 4) and control buttons 132, 134 (FIG. 4) to the imaging module 106.

Figure 5:
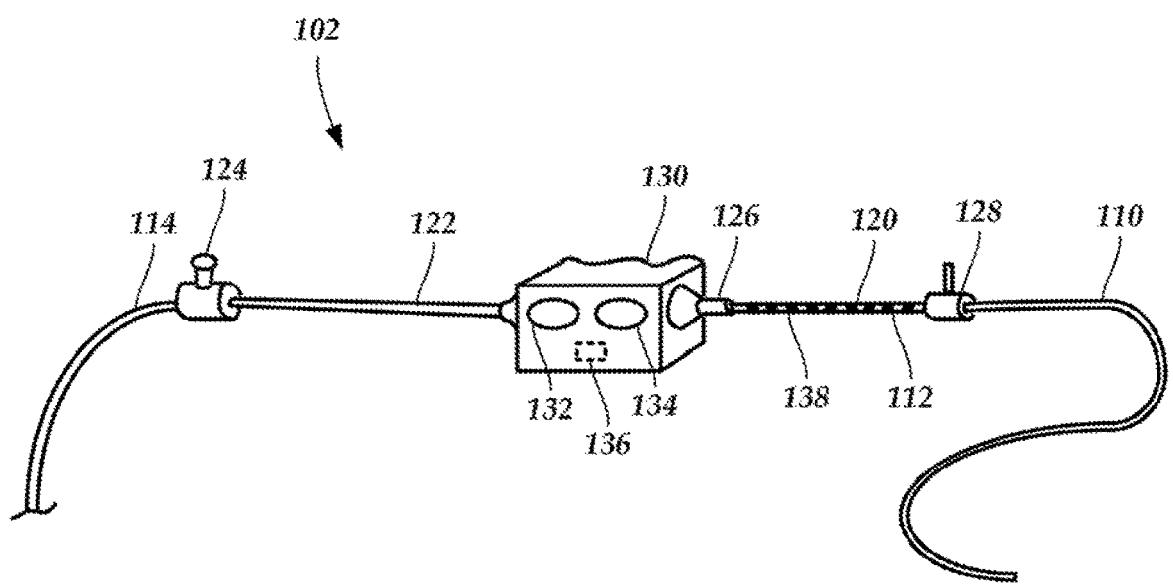
FIG. 5 is a schematic side view of a portion of another embodiment of a catheter with a telescoping pullback section, according to the invention.

FIG. 5 illustrates another embodiment of an IVUS catheter with an integrated pullback sensor. In this embodiment, the proximal grip 130 is disposed between the first telescope 120 and the second telescope 122 and the flush port 124 is disposed between the second telescope 122 and the proximal extension 114. The sensor 136 can be positioned within the proximal grip 130 (as illustrated) or in the housing 126 that coupled the proximal grip 130 to the first telescope 122.

Figure 6A:
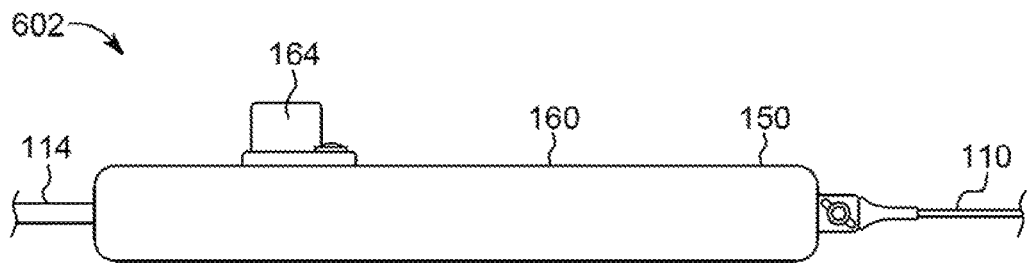
FIG. 6A is a schematic side view of a portion of one embodiment of a catheter with a pullback slider arrangement, according to the invention.
Figure 6B:
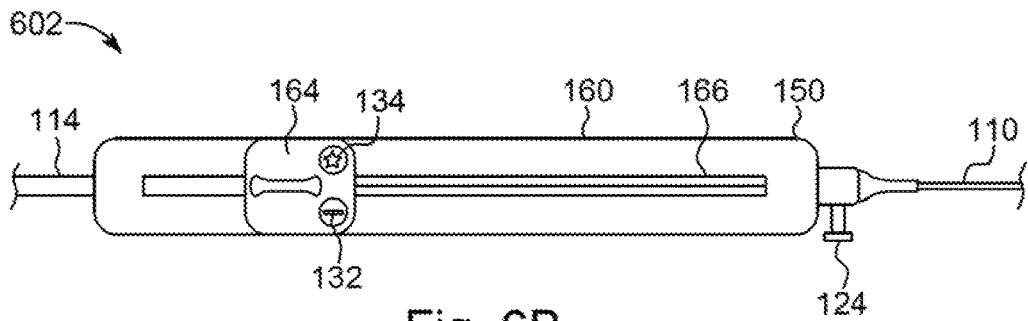
FIG. 6B is a top view of the portion of the catheter of FIG. 6A, according to the invention.
Figure 6C:
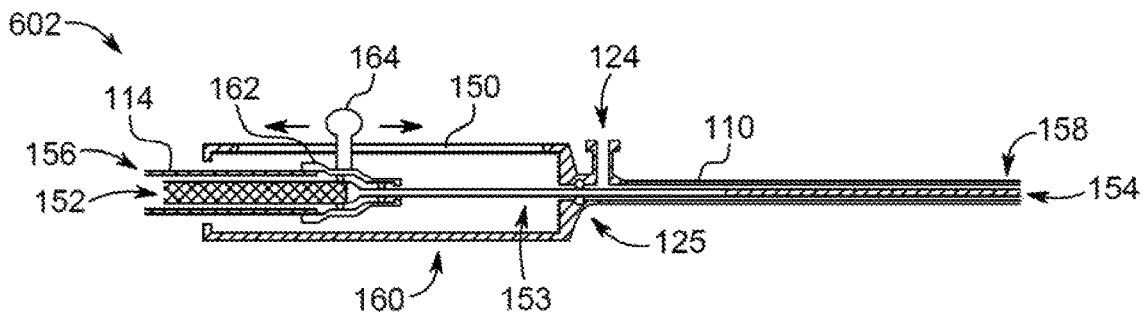
FIG. 6C is a side cross-sectional view of the catheter of FIG. 6A, according to the invention.

FIGS. 6A-6C illustrate a portion of another embodiment of an IVUS catheter 602 with an integrated pullback arrangement. In this arrangement, the catheter includes a pullback slider arrangement 150 disposed between the distal section 110 and proximal extension 114 of the IVUS catheter. The proximal extension 114 includes a proximal driveshaft 152 disposed within a proximal sheath 156. The distal section 110 includes a distal driveshaft 154 disposed in a distal sheath 158. The proximal and distal driveshafts 152, 154 are coupled together. In the illustrated embodiment, the proximal and distal driveshafts 152, 154 are coupled together within the pullback slider arrangement 150 using an optional intermediate driveshaft 153 (such as a hypotube).

The pullback slider arrangement 150 includes a housing 160 defining a slot 166 through the housing, a coupler 162 within the housing, and a slider handle 164 attached to the coupler and extending out of the housing. The coupler 162 is coupled to one or both of the proximal or distal driveshafts 152, 154 to move the driveshafts 152, 154 while still allowing the driveshafts 152, 154 to rotate within the coupler and housing 160. The coupler 162 may be attached to the proximal sheath 156 as illustrated in FIG. 6C, and may include bearings or other suitable components for coupling to one or both of the driveshafts. By manually moving the slider handle 164 along the slot 166 in the housing, the distal driveshaft 154 (and the imaging device attached to the distal end of the driveshaft) is moved. A pullback procedure can be performed by pulling the slider handle 164 along the slot 166 away from the distal section 110 of the catheter.

In at least some embodiments, the distal section 110 can be flushed with sterile saline via a port 124 on the pullback slider arrangement 150 or distal section 110. The housing 160 which optionally contains a seal 125 to allow flushing without leakage of the saline.

The slider handle 164 or housing 160 may also incorporate one or more control buttons 132, 134. The control buttons 132, 134 may be operated during pullback to individually control functions such as "imaging start/stop", "pullback recording start/stop", "zero position", or "place bookmark".

Pullback position measurement for the catheter 602 may be accomplished using any suitable sensor and method of measurement. It will also be understood the sensors and methods described below can also be incorporated into the catheter 102 of FIGS. 4 and 5.

Figure 7:
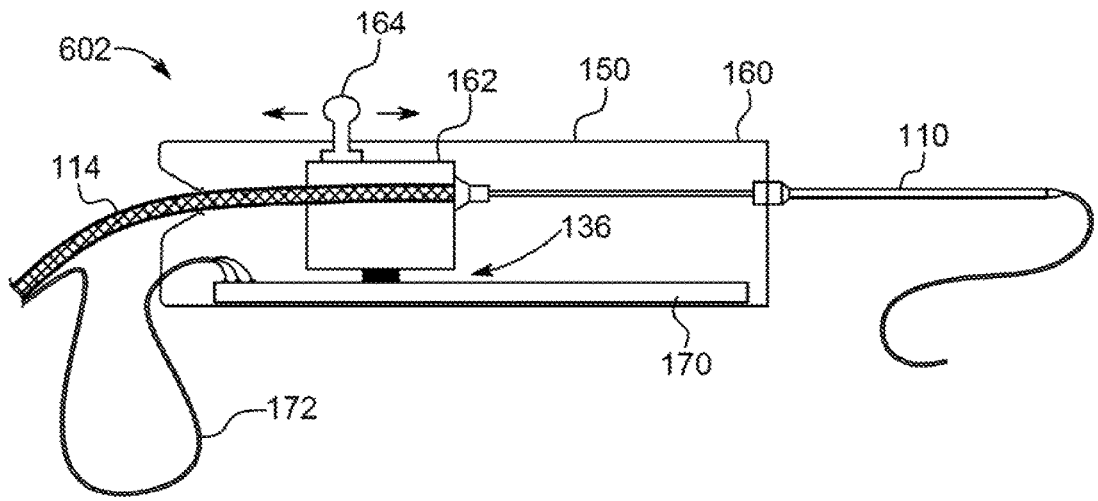
FIG. 7 is a schematic cross-sectional view of a portion of a second embodiment of a catheter with a pullback slider arrangement and a resistive sensor, according to the invention.

FIG. 7 illustrates one embodiment of a resistive sensor 136 used in a potentiometer configuration in which a voltage is generated that is proportional to the coupler 162 position. This can be accomplished using, for example, a slide potentiometer like those used to control signal levels on, for example, an audio mixing desk. The slide potentiometer 170 is actuated using the coupler 162 and slider handle 164. Conductors 172 from the potentiometer can be coupled to the imaging module 106 (FIG. 1) and may be separate from the proximal extension 114 or run along or within the sheath 156 of the proximal extension 114 or in any other suitable arrangement.

Figure 8:
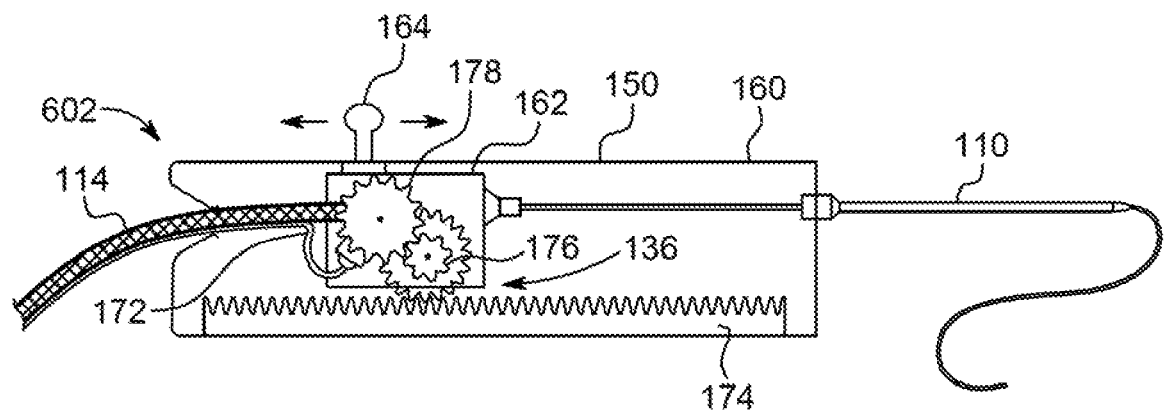
FIG. 8 is a schematic cross-sectional view of a portion of a third embodiment of a catheter with a pullback slider arrangement and a rotary resistive sensor, according to the invention.

FIG. 8 illustrates another embodiment of a resistive sensor 136 using a rotary potentiometer. The potentiometer is rotated using a rack 174, a pinion 176, and one or more optional reduction gears 178 to form a rotary potentiometer. Conductors 172 from the potentiometer can be coupled to the imaging module 106 (FIG. 1) and may be separate from the proximal extension 114 or run along or within the sheath 156 of the proximal extension 114 or in any other suitable arrangement.

In at least some embodiments, the potentiometer configurations of FIGS. 7 and 8 use three wires to operate. However, other resistive sensor can be used that measures a resistance in proportion to position and would only use two wires.

Figure 9:
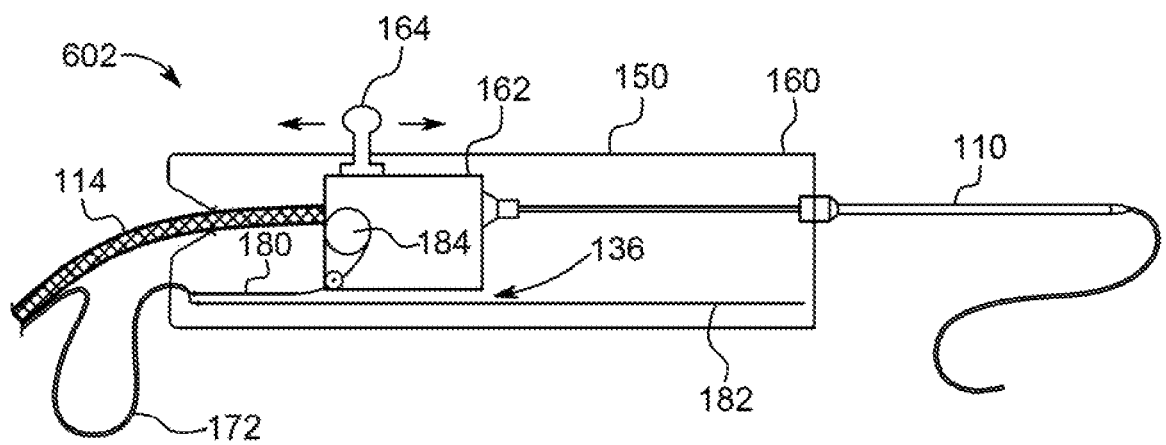
FIG. 9 is a schematic cross-sectional view of a portion of a fourth embodiment of a catheter with a pullback slider arrangement and a capacitive sensor, according to the invention.

FIG. 9 illustrates one embodiment of a capacitive sensor 136 that includes a top plate 180 and a bottom plate 182 that overlap over a distance defined by the position of the coupler 162 to form a variable capacitor. Excess length of the top plate 180 is taken up on a roller 184 (for example, a spring loaded or "windowshade" roller). This configuration produces a capacitance that varies with pullback position. Conductors 172 from the sensor can be coupled to the imaging module 106 (FIG. 1) and may be separate from the proximal extension 114 or run along or within the sheath 156 of the proximal extension 114 or in any other suitable arrangement. Again, as with the resistive sensor, a geared rotary variable capacitor could also be used.

Figure 10:
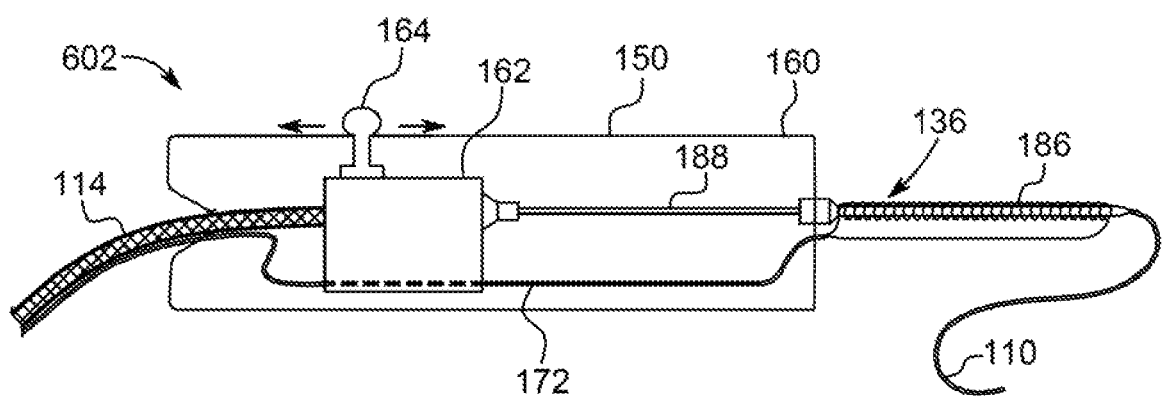
FIG. 10 is a schematic cross-sectional view of a portion of a fifth embodiment of a catheter with a pullback slider arrangement and an inductive sensor, according to the invention.

FIG. 10 illustrate one embodiment of an inductive sensor 136 that includes a coil 186 around a portion of the distal sheath 158 (FIG. 6C) with a highly magnetic material 188 embedded in a portion of the rotating driveshaft 153, 154 (FIG. 6C) or a rotating sheath (not shown) on the driveshaft. In this way, the inductance of coil 186 would vary as the magnetic material 188 is slid in or out of the sheath 158. The inductance varies in a predictable way with the overlap distance between the coil 186 and magnetic material 188.

Conductors 172 from the sensor can be coupled to the imaging module 106 (FIG. 1) and may be separate from the proximal extension 114 or run along or within the sheath 156 of the proximal extension 114 or in any other suitable arrangement. Again, as with the resistive sensor, a geared rotary variable capacitor could also be used.

Capacitive and inductive sensors may be operated at some RF frequency (for example, about 10 to 100 MHz) for purposes of measuring their position-variable capacitance or inductance values. In some alternative embodiments, it may be advantageous if the ultrasound transmitting and receiving electronics are used to interrogate the sensor. For example, a variable inductance sensor could be coupled in parallel to a fixed capacitor and then the combination placed in parallel with the transducer's RF transmission line. If the resonant frequency of the sensor is designed to be far from the transducer frequency (say, using a 10 MHz sensor with a 40 MHz transducer) then the sensor can be interrogated by issuing a carefully designed transmit pulse between imaging periods. The sensor inductance (and therefore the pullback position) can be inferred from the resonant frequency of the LC circuit. This configuration has an advantage that no additional wiring may be needed for the pullback sensor instead of including the conductors 172 illustrated in FIGS. 9 and 10. On the other hand, such an arrangement may not be able to produce an accurate position measurement without distorting the imaging signals.

Figure 11:
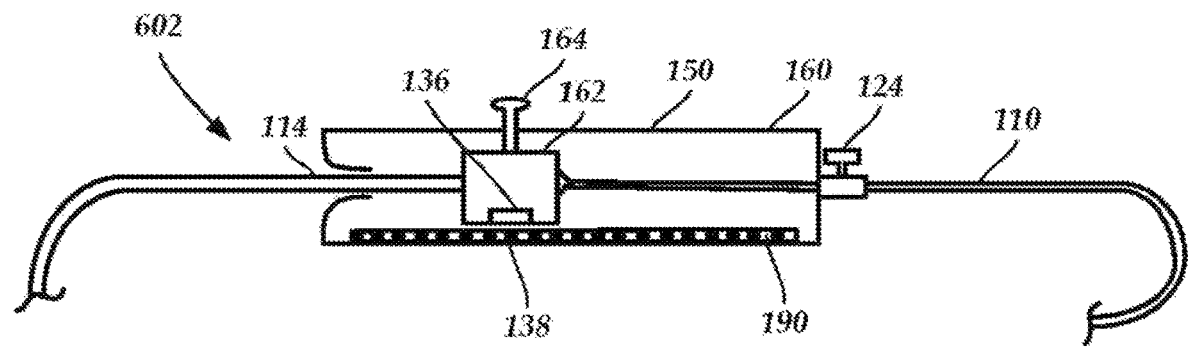
FIG. 11 is a schematic cross-sectional view of a portion of a sixth embodiment of a catheter with a pullback slider arrangement and a magnetic or optical sensor, according to the invention.

FIG. 11 illustrates one embodiment of a magnetic or optical sensor 136. In some embodiments, the sensor 136 is a magnetic sensor (for example, a quadrature magneto-resistive sensor (such as the MLS1000HD, available from Measurement Specialties™, Inc./TE Sensor Solutions of Middletown, PA)). The sensor 136 reads magnetic stripes 138 manufactured with a well-defined pitch on a strip 190 disposed in the housing 160. Alternatively, the sensor 136 is an optical sensor that reads black and white (or any other differentiable colors) stripes 138 on the strip 190. A pair of such sensors 136 (quadrature sensors) could be used to enable the direction of position movement to be detected. As with the resistive sensor, a geared rotary optical or magnetic sensor could also be used. Conductors from the sensor 136 can be coupled to the imaging module 106 (FIG. 1) and may be separate from the proximal extension 114 or run along or within the sheath of the proximal extension 114 or in any other suitable arrangement.

Figure 12:
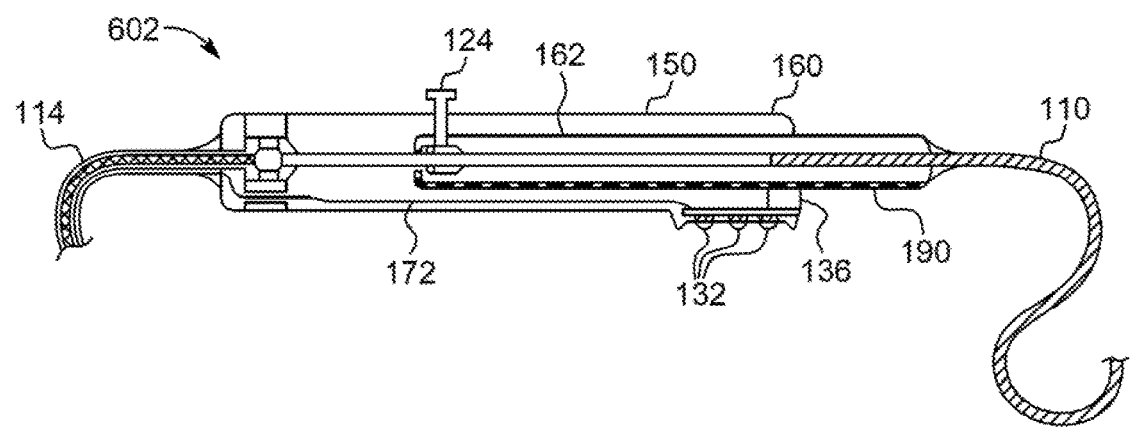
FIG. 12 is a schematic cross-sectional view of a portion of a seventh embodiment of a catheter with a pullback slider arrangement and a magnetic or optical sensor, according to the invention.

FIG. 12 illustrates another embodiment using a magnetic or optical sensor 136. In this embodiment, a housing 160 is affixed to the proximal extension 114. The proximal extension also contains conductors 172 for the position sensor 136. The distal section 110 extends into a coupler 162 that also includes a seal and flush port 124 disposed extending out of a slot (not shown) in the housing 160. The coupler 162 also contains a strip 190 which is situated so it can communicate with the position sensor 136 in the housing 160. The sensor 136 can be a magnetic sensor that reads magnetic stripes on the strip 190 or an optical sensor that reads black and white (or any other differentiable colors) stripes on the strip 190.

The sensors 136 described above can be used to determine a position of the imaging core during a pullback or other procedure and can be used to align resulting imaging data. It will be understood that the sensors 136 can also be used in conjunction with an automated pullback device to also determine position of the imaging core during an automated pullback procedure.

Pullback is performed by gripping the housing 160 in one hand and the distal end of the coupler 162 in the other hand and pulling back the coupler (or pushing forward the housing). Alternatively, the flush port 124 may be used to slide the coupler 162 backwards.

Several of these embodiments illustrate one or more conductors 172 coupling the sensor 136 to the imaging module 106 (FIG. 1) directly or via the motordrive 104 (FIG. 1) or the imaging module 106 (FIG. 1). Alternatively or additionally, wireless communication can be used between the imaging module 106 and the sensor 136 using Bluetooth™ or other wireless technologies. Alternatively or additionally, a wired connection may be provided between the sensor 136 and the motordrive 104 with wireless communication between the motordrive and the imaging module 106. Similar methods of wired or wireless (or combination thereof) communication can be used between the control buttons 132, 134 and the imaging module 106. The housing 160 may also incorporate one or more control buttons 132. The control buttons 132 may be operated during pullback to individually control functions such as "imaging start/stop", "pullback recording start/stop", "zero position", or "place bookmark". It will be recognized that similar control buttons can be used on any of the embodiments described above. Moreover, it will be recognized that this embodiment can be modified to use any of the other sensors described above.

As indicated above, the IVUS imaging system is capable of recording multiple ultrasound frames while the imaging core is pulled back inside the distal sheath. The resulting data set (a longview data set) can represent a 3D view of a section of the anatomy where the imaging catheter is disposed. In conventional IVUS imaging systems, a longview data set is acquired using a motorized pullback at a constant velocity (for example, about 0.5 or 1 mm/sec). IVUS frames are recorded at constant intervals (for example, 30 frames/sec), so the frames may be positioned accurately within the longview data set. Pullback velocities of 0.5 or 1 mm/sec, coupled with a frame capture rate of 30 frames/sec, produce a longview resolution of 30 or 60 frames/mm.

For a manual pullback procedure, as described above, the sensor can be used to determine correct frame positioning to produce a longview data set regardless of pullback speed or variability during the manual pullback procedure. In at least some embodiments, an IVUS imaging system is configured to recognize a "pullback" operation as different from a "push forward" operation and IVUS frames are only acquired during a pullback procedure. Such an arrangement may reduce or eliminate a problem of "backlash" in the pullback system and facilitate correct position measurements. If there were no backlash in the mechanical system, it can be possible to record longview IVUS frames during pullback or push forward.

One embodiment of a method for producing a longview data set during a manual pullback procedure can include the following steps: 1. A control button (e.g., control buttons 132, 134 in FIG. 4, 5, or 6B) is pressed on the catheter or imaging module, or a command is issued, to the imaging module 106 to initiate a recording of IVUS data (e.g., a longview recording.)

2. The imaging core is pulled back (for example, at a moderate to high speed, such as 10 to 30 mm/sec) and the system acquires IVUS frames to produce a longview data set with relatively low resolution (for example, 1 to 3 frames per mm with a frame capture rate of 30 frames/sec). In at least some embodiments, the clinician may stop pulling back and then pushes the imaging core forward to revisit a region of interest (ROI) in the anatomy. The system does not acquire IVUS frames during the push forward. In some embodiments, the region of the pullback recording that has been pushed back over may be colored or otherwise marked in the IVUS display to denote that it may be overwritten during the next pullback operation.

3. After the imaging core is repositioned distal to the ROI, manual pullback is resumed at, for example, a slower speed (such as 0.5 to 5 mm/sec) and the system recognizes that pullback has been resumed and responds by reacquiring frames over the ROI. In at least some embodiments, the longview data set is repainted over the ROI at a greater longview resolution (about 6 to 60 frames/mm). Acquisition may also be paused or restarted by pressing a control button (e.g., control buttons 132, 134 in FIG. 4, 5, or 6B) on the catheter or the imaging module. This feature allows reexamination of portions of the anatomy without rerecording pullback data if so desired.

4. The IVUS imaging system is commanded to end the pullback recording operation by pressing another control button (e.g., control buttons 132, 134 in FIG. 4, 5, or 6B) on the catheter or the imaging module. The recorded pullback data set is then available for review or archiving. The resulting longview data set may contain regions with varying longview resolution (frames/mm). The frames are correctly positioned along the longview axis because accurate position data from the sensor were acquired along with the IVUS frames.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A catheter assembly for an ultrasound system, the catheter assembly comprising:
    a distal section comprising a distal sheath;
    a proximal extension comprising a proximal sheath;
    a telescoping pullback section including a first telescope and a second telescope;
    a pullback slider arrangement disposed between the distal section and the proximal extension, the pullback slider arrangement comprising a housing defining a slit, a coupler disposed within the housing, and a slider handle coupled to the coupler within the housing and extending through the slit such that a portion of the slider handle is disposed along an exterior of the housing, wherein the slider handle and the coupler can be manually slid along the slit in the housing;
    a sensor disposed within the housing of the pullback slider arrangement to determine a position of the coupler within the housing and to determine the position of the first telescope relative to the second telescope;
    an elongated, rotatable driveshaft having a proximal end and a distal end and extending along the distal section, the proximal extension, and the pullback slider arrangement, wherein the proximal end is configured and arranged for coupling to a motordrive for rotating the driveshaft, wherein the coupler of the pullback slider arrangement is coupled to the rotatable driveshaft to manually move the rotatable driveshaft backwards and forwards by moving the slider handle;
    wherein the rotatable driveshaft is coupled to the first telescope;
    wherein the rotatable driveshaft includes a proximal driveshaft coupled to a proximal end region of the coupler, an intermediate shaft coupled to a distal end region of the coupler, and a distal driveshaft coupled to the intermediate shaft;
    an imaging device coupled to the distal end of the driveshaft with rotation of the driveshaft causing a corresponding rotation of the imaging device, the imaging device comprising at least one transducer configured and arranged for transforming applied electrical signals to acoustic signals and also for transforming received echo signals to electrical signals; and
    at least one conductor extending along the distal section, the proximal extension, and the coupler and coupled to the imaging device for carrying the electrical signals.

2. The catheter assembly of claim 1, wherein the housing of the pullback slider arrangement comprises a control button, wherein actuation of the control button provides a signal related to a pullback procedure.

3. The catheter assembly of claim 1, wherein the sensor is an optical, resistive, capacitive, inductive, or magnetic sensor.

4. The catheter assembly of claim 1, wherein the sensor is a potentiometer.

5. The catheter assembly of claim 1, wherein the sensor is a capacitive sensor and comprises a first plate and a second plate that is coupled to the coupler of the pullback slider arrangement so that capacitance between the first and second plates varies with position of the coupler.

6. The catheter assembly of claim 1, wherein the sensor is an inductive sensor and comprises a coil and a magnetic material that is coupled to the coupler of the pullback slider arrangement and moves with the coupler so that inductance of the coil varies with position of the coupler.

7. The catheter assembly of claim 1, wherein the sensor is an optical sensor coupled to the coupler and the pullback slider arrangement comprises a set of alternating stripes of different colors detectable by the optical sensor and disposed in the housing to determine a position of the coupler.

8. The catheter assembly of claim 1, wherein the sensor is a magnetic sensor coupled to the coupler and the pullback slider arrangement comprises a set of alternating stripes of magnetic materials detectable by the magnetic sensor and disposed in the housing to determine a position of the coupler.

9. The catheter assembly of claim 1, wherein the slider handle comprises at least one control button, wherein actuation of one of the at least one control button provides a signal related to a pullback procedure.

10. The catheter assembly of claim 1, wherein the sensor is a magnetic sensor coupled to the housing and the pullback slider arrangement comprises a set of alternating stripes of magnetic materials detectable by the magnetic sensor and disposed on the coupler to determine a position of the coupler.

* * * * *